(12) United States Patent
Grote et al.

(10) Patent No.: US 6,670,327 B1
(45) Date of Patent: Dec. 30, 2003

(54) THERAPEUTIC USES OF BPI PROTEIN PRODUCTS IN HUMANS WITH OTITIS MEDIA WITH EFFUSION

(75) Inventors: Jan J. Grote, RC Leiden (NL); Maartje J. Nell, RC Leiden (NL)

(73) Assignee: Xoma (US) LLC, Berkeley, CA (US)

( * ) Notice: Subject to any disclaimer, the term of this patent is extended or adjusted under 35 U.S.C. 154(b) by 0 days.

(21) Appl. No.: 09/586,850

(22) Filed: Jun. 5, 2000

(Under 37 CFR 1.47)

Related U.S. Application Data

(63) Continuation of application No. PCT/US00/14496, filed on May 24, 2000.
(60) Provisional application No. 60/136,148, filed on May 24, 1999.

(51) Int. Cl.[7] .............................................. A61K 38/00
(52) U.S. Cl. ...................................................... 514/12
(58) Field of Search ............................ 530/412; 514/12, 514/222.2

(56) References Cited

U.S. PATENT DOCUMENTS

| | | | |
|---|---|---|---|
| 5,171,739 A | * 12/1992 | Scott et al. .................... | 514/12 |
| 5,198,541 A | 3/1993 | Elsbach et al. | |
| 6,013,631 A | * 1/2000 | Horwitz et al. ................ | 514/12 |
| 6,121,427 A | * 9/2000 | Yang et al. ............... | 424/184.1 |
| 6,350,742 B1 | * 2/2002 | Costin ...................... | 514/222.2 |

OTHER PUBLICATIONS

Horwitz et al. Expression and characterization of cysteine–modified variants of an amino–terminal fragment of bactericidal/permeability–increasing protein. Protein Expr Purif. Aug. 1996;8(1):28–40.*

Miller et al., "Bacterial Antigens and Neutrophil Granule Proteins in Middle Ear Effusions" Arch Otolaryngol Head Neck Surg 116:335–337 (1990).

Nell et al., "Bacterial/Permeability–Increasing Protein Prevents Mucosal Damage in an Experimental Rat Model of Chronic Otitis Media with Effusion" Infection and Immunity 68:2992–2994 (2000).

Nell et al., "Inhibition of Endotoxin Effects on Cultured Human Middle Ear Epithelium by Bactericidal Permeability–Increasing Protein" The American Journal of Otology 21:625–630 (2000).

* cited by examiner

Primary Examiner—Karen Cochrane Carlson
Assistant Examiner—Sheridan Snedden
(74) Attorney, Agent, or Firm—Marshall, Gerstein & Borun LLP

(57) ABSTRACT

New therapeutic uses for BPI protein products for treating otitis media with effusion in humans are provided.

6 Claims, No Drawings

SEQUENCE LISTING

```
<160> NUMBER OF SEQ ID NOS:  2

<210> SEQ ID NO 1
<211> LENGTH: 1813
<212> TYPE: DNA
<213> ORGANISM: Homo sapiens
<220> FEATURE:
<221> NAME/KEY: CDS
<222> LOCATION: (31)..(1491)
<221> NAME/KEY: mat_peptide
<222> LOCATION: (124)..(1491)

<400> SEQUENCE: 1
caggccttga ggttttggca gctctggagg atg aga gag aac atg gcc agg ggc        54
                                 Met Arg Glu Asn Met Ala Arg Gly
                                     -30                 -25 cct tgc aac gcg ccg aga tgg gtg tcc ctg atg gtg ctc gtc gcc ata       102
Pro Cys Asn Ala Pro Arg Trp Val Ser Leu Met Val Leu Val Ala Ile
      -20                 -15                 -10
```

```
ggc acc gcc gtg aca gcg gcc gtc aac cct ggc gtc gtg gtc agg atc     150
Gly Thr Ala Val Thr Ala Ala Val Asn Pro Gly Val Val Val Arg Ile
        -5              -1  1               5 tcc cag aag ggc ctg gac tac gcc agc cag cag ggg acg gcc gct ctg     198
Ser Gln Lys Gly Leu Asp Tyr Ala Ser Gln Gln Gly Thr Ala Ala Leu
 10              15                  20                  25 cag aag gag ctg aag agg atc aag att cct gac tac tca gac agc ttt     246
Gln Lys Glu Leu Lys Arg Ile Lys Ile Pro Asp Tyr Ser Asp Ser Phe
             30                  35                  40 aag atc aag cat ctt ggg aag ggg cat tat agc ttc tac agc atg gac     294
Lys Ile Lys His Leu Gly Lys Gly His Tyr Ser Phe Tyr Ser Met Asp
                 45                  50                  55 atc cgt gaa ttc cag ctt ccc agt tcc cag ata agc atg gtg ccc aat     342
Ile Arg Glu Phe Gln Leu Pro Ser Ser Gln Ile Ser Met Val Pro Asn
                     60                  65                  70 gtg ggc ctt aag ttc tcc atc agc aac gcc aat atc aag atc agc ggg     390
Val Gly Leu Lys Phe Ser Ile Ser Asn Ala Asn Ile Lys Ile Ser Gly
         75                  80                  85 aaa tgg aag gca caa aag aga ttc tta aaa atg agc ggc aat ttt gac     438
Lys Trp Lys Ala Gln Lys Arg Phe Leu Lys Met Ser Gly Asn Phe Asp
 90              95                 100                 105 ctg agc ata gaa ggc atg tcc att tcg gct gat ctg aag ctg ggc agt     486
Leu Ser Ile Glu Gly Met Ser Ile Ser Ala Asp Leu Lys Leu Gly Ser
                110                 115                 120 aac ccc acg tca ggc aag ccc acc atc acc tgc tcc agc tgc agc agc     534
Asn Pro Thr Ser Gly Lys Pro Thr Ile Thr Cys Ser Ser Cys Ser Ser
            125                 130                 135 cac atc aac agt gtc cac gtg cac atc tca aag agc aaa gtc ggg tgg     582
His Ile Asn Ser Val His Val His Ile Ser Lys Ser Lys Val Gly Trp
        140                 145                 150 ctg atc caa ctc ttc cac aaa aaa att gag tct gcg ctt cga aac aag     630
Leu Ile Gln Leu Phe His Lys Lys Ile Glu Ser Ala Leu Arg Asn Lys
    155                 160                 165 atg aac agc cag gtc tgc gag aaa gtg acc aat tct gta tcc tcc aag     678
Met Asn Ser Gln Val Cys Glu Lys Val Thr Asn Ser Val Ser Ser Lys
170                 175                 180                 185 ctg caa cct tat ttc cag act ctg cca gta atg acc aaa ata gat tct     726
Leu Gln Pro Tyr Phe Gln Thr Leu Pro Val Met Thr Lys Ile Asp Ser
                190                 195                 200 gtg gct gga atc aac tat ggt ctg gtg gca cct cca gca acc acg gct     774
Val Ala Gly Ile Asn Tyr Gly Leu Val Ala Pro Pro Ala Thr Thr Ala
            205                 210                 215 gag acc ctg gat gta cag atg aag ggg gag ttt tac agt gag aac cac     822
Glu Thr Leu Asp Val Gln Met Lys Gly Glu Phe Tyr Ser Glu Asn His
        220                 225                 230 cac aat cca cct ccc ttt gct cca cca gtg atg gag ttt ccc gct gcc     870
His Asn Pro Pro Pro Phe Ala Pro Pro Val Met Glu Phe Pro Ala Ala
    235                 240                 245 cat gac cgc atg gta tac ctg ggc ctc tca gac tac ttc ttc aac aca     918
His Asp Arg Met Val Tyr Leu Gly Leu Ser Asp Tyr Phe Phe Asn Thr
250                 255                 260                 265 gcc ggg ctt gta tac caa gag gct ggg gtc ttg aag atg acc ctt aga     966
Ala Gly Leu Val Tyr Gln Glu Ala Gly Val Leu Lys Met Thr Leu Arg
                270                 275                 280 gat gac atg att cca aag gag tcc aaa ttt cga ctg aca acc aag ttc    1014
Asp Asp Met Ile Pro Lys Glu Ser Lys Phe Arg Leu Thr Thr Lys Phe
            285                 290                 295 ttt gga acc ttc cta cct gag gtg gcc aag aag ttt ccc aac atg aag    1062
Phe Gly Thr Phe Leu Pro Glu Val Ala Lys Lys Phe Pro Asn Met Lys
```

-continued

```
              300                 305                 310
ata cag atc cat gtc tca gcc tcc acc ccg cca cac ctg tct gtg cag    1110
Ile Gln Ile His Val Ser Ala Ser Thr Pro Pro His Leu Ser Val Gln
    315                 320                 325 ccc acc ggc ctt acc ttc tac cct gcc gtg gat gtc cag gcc ttt gcc    1158
Pro Thr Gly Leu Thr Phe Tyr Pro Ala Val Asp Val Gln Ala Phe Ala
330                 335                 340                 345 gtc ctc ccc aac tcc tcc ctg gct tcc ctc ttc ctg att ggc atg cac    1206
Val Leu Pro Asn Ser Ser Leu Ala Ser Leu Phe Leu Ile Gly Met His
                350                 355                 360 aca act ggt tcc atg gag gtc agc gcc gag tcc aac agg ctt gtt gga    1254
Thr Thr Gly Ser Met Glu Val Ser Ala Glu Ser Asn Arg Leu Val Gly
            365                 370                 375 gag ctc aag ctg gat agg ctg ctc ctg gaa ctg aag cac tca aat att    1302
Glu Leu Lys Leu Asp Arg Leu Leu Leu Glu Leu Lys His Ser Asn Ile
        380                 385                 390 ggc ccc ttc ccg gtt gaa ttg ctg cag gat atc atg aac tac att gta    1350
Gly Pro Phe Pro Val Glu Leu Leu Gln Asp Ile Met Asn Tyr Ile Val
    395                 400                 405 ccc att ctt gtg ctg ccc agg gtt aac gag aaa cta cag aaa ggc ttc    1398
Pro Ile Leu Val Leu Pro Arg Val Asn Glu Lys Leu Gln Lys Gly Phe
410                 415                 420                 425 cct ctc ccg acg ccg gcc aga gtc cag ctc tac aac gta gtg ctt cag    1446
Pro Leu Pro Thr Pro Ala Arg Val Gln Leu Tyr Asn Val Val Leu Gln
                430                 435                 440 cct cac cag aac ttc ctg ctg ttc ggt gca gac gtt gtc tat aaa         1491
Pro His Gln Asn Phe Leu Leu Phe Gly Ala Asp Val Val Tyr Lys
            445                 450                 455 tgaaggcacc aggggtgccg ggggctgtca gccgcacctg ttcctgatgg gctgtggggc   1551
accggctgcc tttccccagg gaatcctctc cagatcttaa ccaagagccc cttgcaaact   1611
tcttcgactc agattcagaa atgatctaaa cacgaggaaa cattattcat tggaaaagtg   1671
catggtgtgt attttaggga ttatgagctt cttcaaggg ctaaggctgc agagatattt    1731
cctccaggaa tcgtgtttca attgtaacca agaaatttcc atttgtgctt catgaaaaaa   1791
aacttctggt ttttttcatg tg                                            1813
```

<210> SEQ ID NO 2
<211> LENGTH: 487
<212> TYPE: PRT
<213> ORGANISM: Homo sapiens

<400> SEQUENCE: 2

```
Met Arg Glu Asn Met Ala Arg Gly Pro Cys Asn Ala Pro Arg Trp Val
    -30                 -25                 -20

Ser Leu Met Val Leu Val Ala Ile Gly Thr Ala Val Thr Ala Ala Val
-15                 -10                 -5                  -1   1

Asn Pro Gly Val Val Arg Ile Ser Gln Lys Gly Leu Asp Tyr Ala
                5                  10                  15

Ser Gln Gln Gly Thr Ala Ala Leu Gln Lys Glu Leu Lys Arg Ile Lys
            20                  25                  30

Ile Pro Asp Tyr Ser Asp Ser Phe Lys Ile Lys His Leu Gly Lys Gly
        35                  40                  45

His Tyr Ser Phe Tyr Ser Met Asp Ile Arg Glu Phe Gln Leu Pro Ser
50                  55                  60                  65

Ser Gln Ile Ser Met Val Pro Asn Val Gly Leu Lys Phe Ser Ile Ser
                70                  75                  80
```

-continued

```
Asn Ala Asn Ile Lys Ile Ser Gly Lys Trp Lys Ala Gln Lys Arg Phe
            85                  90                  95

Leu Lys Met Ser Gly Asn Phe Asp Leu Ser Ile Glu Gly Met Ser Ile
           100                 105                 110

Ser Ala Asp Leu Lys Leu Gly Ser Asn Pro Thr Ser Gly Lys Pro Thr
           115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
            150                 155                 160

Ile Glu Ser Ala Leu Arg Asn Lys Met Asn Ser Gln Val Cys Glu Lys
            165                 170                 175

Val Thr Asn Ser Val Ser Ser Lys Leu Gln Pro Tyr Phe Gln Thr Leu
            180                 185                 190

Pro Val Met Thr Lys Ile Asp Ser Val Ala Gly Ile Asn Tyr Gly Leu
            195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Phe Ala Pro
            230                 235                 240

Pro Val Met Glu Phe Pro Ala Ala His Asp Arg Met Val Tyr Leu Gly
            245                 250                 255

Leu Ser Asp Tyr Phe Phe Asn Thr Ala Gly Leu Val Tyr Gln Glu Ala
            260                 265                 270

Gly Val Leu Lys Met Thr Leu Arg Asp Asp Met Ile Pro Lys Glu Ser
            275                 280                 285

Lys Phe Arg Leu Thr Thr Lys Phe Phe Gly Thr Phe Leu Pro Glu Val
290                 295                 300                 305

Ala Lys Lys Phe Pro Asn Met Lys Ile Gln Ile His Val Ser Ala Ser
            310                 315                 320

Thr Pro Pro His Leu Ser Val Gln Pro Thr Gly Leu Thr Phe Tyr Pro
            325                 330                 335

Ala Val Asp Val Gln Ala Phe Ala Val Leu Pro Asn Ser Ser Leu Ala
            340                 345                 350

Ser Leu Phe Leu Ile Gly Met His Thr Thr Gly Ser Met Glu Val Ser
            355                 360                 365

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
            390                 395                 400

Gln Asp Ile Met Asn Tyr Ile Val Pro Ile Leu Val Leu Pro Arg Val
            405                 410                 415

Asn Glu Lys Leu Gln Lys Gly Phe Pro Leu Pro Thr Pro Ala Arg Val
            420                 425                 430

Gln Leu Tyr Asn Val Val Leu Gln Pro His Gln Asn Phe Leu Leu Phe
            435                 440                 445

Gly Ala Asp Val Val Tyr Lys
450                 455
```

THERAPEUTIC USES OF BPI PROTEIN PRODUCTS IN HUMANS WITH OTITIS MEDIA WITH EFFUSION

This application is a continuation of International Application No. PCT/US00/14496 filed May 24, 2000, which claims priority of U.S. Provisional Application Ser. No. 60/136,148 filed May 24, 1999.

The present invention relates generally to novel therapeutic uses of BPI protein products for treatment of otitis media with effusion in humans.

BACKGROUND OF THE INVENTION

Otitis media is the most frequently diagnosed disease in children in the United States, and most children will have at least one episode. It is most common in children under 6 years of age. The term "otitis media" refers to a spectrum of diseases in which fluid (effusion) is present in the middle ear space. The effusion may be serous, mucoid, purulent or some combination of these. In acute otitis media, signs and symptoms of acute infection and inflammation accompany middle ear effusion.

In otitis media with effusion (OME), there is a middle ear effusion behind an intact tympanic membrane without signs or symptoms of acute infection; synonymous terms include "fluid in the ear," "glue ear," and "serous otitis media." OME is defined as chronic when middle ear effusion has been present for at least three months. OME frequently can cause hearing loss at a critical time in a child's development and can interfere with speech, language, behavioral and cognitive development. In most cases, the effusion may resolve spontaneously, but there remain a significant number of children in whom effusion persists even after the acute infection has resolved. Approximately 15% of children have chronic problems with longer term conductive hearing loss and sometimes lasting changes of the eardrum and middle ear ossicles. The complications and sequelae often persist into the adult years.

Persistent effusion, infection or epithelial damage promotes the release of a number of potent inflammatory mediators which, together with numerous bacterial toxins and enzymes present in the effusion, may be stimuli for metaplasia of the middle ear epithelium into a more secretory (mucus-producing) type of epithelium, similar to that found in the lower respiratory tract. The resulting effusion formed in the tympanic cavity will be removed to the pharynx, provided that the mucociliary clearance system (MCS) is functioning normally. The MCS is composed of ciliated cells, secretory cells and a mucus blanket, and propels mucus towards the eustachian tube by means of beating cilia. Mucociliary function can be impaired not only due to lowered ciliary activity but also due to mucus abnormalities. Increased mucus production and altered mucus consistency may seriously affect ciliary beat and coordination.

The two most important factors preceding the development of OME are a gram-negative bacterial infection and a dysfunction of the eustachian tube. Obstruction of the eustachian tube in germ-carrying rats was reported to result in secretory transformation of the epithelium, a phenomenon not observed in germ-free rats. Kuijpers et al., *Histochemical J.* 16:807–18 (1984).

Endotoxin is the lipopolysaccharide (LPS) outer membrane constituent of gram-negative bacteria and is a strong inducer of inflammation. The lipid A portion of LPS, which accounts for the toxic properties of endotoxin, is structurally similar and serologically cross-reacts among many species of gram-negative bacteria. Endotoxin has been found in human middle ear effusions. DeMaria et al., *J. Clin. Microbiol.* 20(1):15–17 (1984); Ovesen et al., *Clin. Otolaryngology* 17:531–4 (1992); and Dingman et al., *J. Clin. Microbiol.*, 36:3417–19 (1998). Inoculation of endotoxin into the middle ear has been shown to induce morphological changes in the mucociliary transport system, although long term effusion was not observed. [Ohashi et al., *Ann. Otol. Rhinol. Laryngol.* 98:479–84 (1989) and Ohashi et al, *Acta Otolaryngol (Stockh)*, 486:149–61 (1991).] Moreover, injection of viable or non-viable *H. influenzae* or its endotoxin has been shown to induce some inflammatory changes. [DeMaria et al., *Ann. Otol. Rhinol. Laryngol* 94 (S120):14–6 (1985) and 93:52 (1984).]

Obstruction of the eustachian tube disables the normal clearance system of the middle ear. The normal middle ear mucosa has a mucociliary clearance system which consists of ciliated cells interspersed with secretory cells. Both the ciliary function and the secretory activity in the tympanic orifice of the middle ear are important for the clearance of the middle ear. During OME this clearance system is often impaired. When an obstruction of the eustachian tube is accompanied by inflammatory changes in the middle ear which lead to dysfunction of the mucociliary clearance system (MCS), an accumulation of fluid in the tympanic cavity occurs.

A model for OME has been developed in which a combination of eustachian tube obstruction (ETO) and endotoxin injection is used to produce structural changes to and dysfunction of the mucociliary clearance system which persists for 12 weeks. [Nell et al., *Eur. Arch. Otorhinolaryngol.*, 256:167–172 (1999).]

Although acute otitis media is typically treated with antibiotic therapy, medical treatment of OME is problematic and has been unsatisfactory. The efficacy of treatment with an antihistamine-decongestant combination has been debated; Daley [*Pediatrics in Review*, 20:85 (1999)] has reported that this therapy is not recommended because these agents are not effective either separately or together. The use of systemic corticosteroids is common, and benefits of this therapy have been demonstrated in several trials, although the risks and side effects of this type of treatment are significant. Sequentially increasing doses of antimicrobial agents and prolonged courses of antibiotic therapy are common treatments but their efficacy has also been debated. Myringotomy with tube placement (through the tympanic membrane) has been shown to reduce the frequency of recurrence of acute otitis media and to improve hearing while the tubes remain in place, but is a surgical procedure requiring general anesthesia. Adenoidectomy is generally not recommended but may be beneficial in children older than 4 years of age with chronic OME. [Shapiro et al., *Postgraduate Medicine*, 97:73 (1995); Klein, *Clin. Infect. Dis.*, 19:823 (1994); Daley, supra.]

A number of other potential therapies, including anti-inflammatory agents, have been tested in various models of otitis media. S-carboxymethylcysteine has been reported to reduce damage to ciliated cells and goblet cell hyperplasia in chinchillas with immune-mediated OME, although it did not inhibit infiltration or prevent release of chemical mediators such as histamine and prostaglandin E2. [Hori et al, *Ann. Otol. Rhinol. Laryngol* 103:567–75 (1994).] Treatment of children with secretory otitis media with hydroxyzine, an anti-histamine, has been reported to reduce the rate of relapse and the amount of histamine present in middle ear effusions. [Theoharides et al., *Int. Arch. Allergy Immunol.*

103:95–101 (1994).] Endotoxin-induced hypertrophic and metaplastic changes of goblet cells in rat nasal respiratory epithelium was reported to be inhibited by intraperitoneal injection of anti-inflammatory drugs. [Takahashi et al., *Ann. Otol. Rhinol. Laryngol* 106:683–7 (1997).] Indomethacin has been reported to inhibit the accumulation of middle ear effusion [Goldie et al., Ann. Otol. Rhinol. LaryngolI 102 (12):954–60 (1993)]. In vitro addition of human monoclonal antibody against endotoxin, HA-1A (Centoxin), to medium supplemented with endotoxin has been reported to partially suppress some of the proliferative and morphological effects of endotoxin on cultured rat middle ear epithelium, although the morphology of epithelium cultured in the presence of HA-1A and endotoxin was still altered. [Grote et al., *Ann. otol. Rhinol. Laryngol* 104:226–230 (1995).]

Children with OME are currently treated with recurrent placement of ventilation tubes and/or with antibiotics. However, the insertion of tubes will only temporarily remove the middle ear effusion, and antibiotics can be effective in eradicating the infection yet do not reduce the accumulation of fluid.

Because of the current lack of satisfactory treatment, including the disadvantages of ventilation tubes and the growing resistance of many bacterial species to antibiotics, there remains a need for new therapies which can prevent the occurrence of OME or more quickly resolve OME once it occurs.

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.,* 254:11000 (1979)] or *E. coli* affinity chromatography [Weiss, et al., *Blood,* 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., *J. Biol. Chem.,* 264:9505 (1989), incorporated herein by reference. The Gray et al. amino acid sequence is set out in SEQ ID NO: 1 hereto. U.S. Pat. No. 5,198,541 discloses recombinant genes encoding and methods for expression of BPI proteins, including BPI holoprotein and fragments of BPI.

BPI is a strongly cationic protein. The N-terminal half of BPI accounts for the high net positive charge; the C-terminal half of the molecule has a net charge of −3. [Elsbach and Weiss (1981), supra.] A proteolytic N-terminal fragment of BPI having a molecular weight of about 25 kD possesses essentially all the anti-bacterial efficacy of the naturally-derived 55 kD human BPI holoprotein. [Ooi et al., *J. Bio. Chem.,* 262: 14891–14894 (1987)]. In contrast to the N-terminal portion, the C-terminal region of the isolated human BPI protein displays only slightly detectable anti-bacterial activity against gram-negative organisms. [Ooi et al., *J. Exp. Med.* 174:649 (1991).] An N-terminal BPI fragment of approximately 23 kD, referred to as "rBPI$_{23}$," has been produced by recombinant means and also retains anti-bacterial activity against gram-negative organisms. [Gazzano-Santoro et al., *Infect. Immun.* 60:4754–4761 (1992).] An N-terminal analog of BPI, rBPI$_{21}$, has been produced as described in Horwitz et al., *Protein Expression Purification,* 8:28–40 (1996).

The bactericidal effect of BPI was originally reported to be highly specific to gram-negative species, e.g., in Elsbach and Weiss, *Inflammation: Basic Principles and Clinical Correlates*, eds. Gallin et al., Chapter 30, Raven Press, Ltd. (1992). The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

BPI protein products have a wide variety of beneficial activities. BPI protein products are bactericidal for gram-negative bacteria, as described in U.S. Pat. Nos. 5,198,541 and 5,523,288, both of which are incorporated herein by reference. International Publication No. WO 94/20130 (incorporated herein by reference) proposes methods for treating subjects suffering from an infection (e.g. gastrointestinal) with a species from the gram-negative bacterial genus Helicobacter with BPI protein products. BPI protein products also enhance the effectiveness of antibiotic therapy in gram-negative bacterial infections, as described in U.S. Pat. No. 5,523,288 and International Publication No. WO 95/08344 (PCT/US94/11255), which are incorporated herein by reference. BPI protein products are also bactericidal for gram-positive bacteria and mycoplasma, and enhance the effectiveness of antibiotics in gram-positive bacterial infections, as described in U.S. Pat. Nos. 5,578,572 and 5,783,561 and International Publication No. WO 95/19180 (PCT/US95/00656), which are incorporated herein by reference. BPI protein products exhibit anti-fungal activity, and enhance the activity of other anti-fungal agents, as described in U.S. Pat. No. 5,627,153 and International Publication No. WO 95/19179 (PCT/US95/00498), and further as described for anti-fungal peptides in U.S. Pat. No. 5,858,974, which is in turn a continuation-in-part of U.S. application Ser. No. 08/504,841 filed Jul. 20, 1994 and corresponding International Publication Nos. WO 96/08509 (PCT/US95/09262) and WO 97/04008 (PCT/US96/03845), all of which are incorporated herein by reference. BPI protein products exhibit anti-protozoan activity, as described in U.S. Pat. No. 5,646,114 and International Publication No. WO 96/01647 (PCT/US95/08624), which are incorporated herein by reference. BPI protein products exhibit anti-chlamydial activity, as described in co-owned, co-pending U.S. application Ser. No. 08/694,843 filed Aug. 9, 1996 and WO 98/06415 (PCT/US97/13810), which are incorporated herein by reference. Finally, BPI protein products exhibit anti-mycobacterial activity, as described in co-owned, co-pending U.S. application Ser. No. 08/626,646 filed Apr. 1, 1996, which is in turn a continuation of U.S. application Ser. No. 08/285,803 filed Aug. 14, 1994, which is in turn a continuation-in-part of U.S. application Ser. No. 08/031,145 filed Mar. 12, 1993 and corresponding International Publication No. WO94/20129 (PCT/US94/02463), all of which are incorporated herein by reference.

The effects of BPI protein products in humans with endotoxin in circulation, including effects on TNF, IL-6 and endotoxin are described in U.S. Pat. No. 5,643,875, which is incorporated herein by reference.

BPI protein products are also useful for treatment of specific disease conditions, such as meningococcemia in humans (as described in co-owned, co-pending U.S. application Ser. No. 08/644,287 filed May 10, 1996 and continuation Ser. No. 08/927,437 filed Sep. 10, 1997 and International Publication No. WO97/42966 (PCT/US97/08016), all of which are incorporated herein by reference), hemorrhagic trauma in humans, (as described in U.S. Pat. No. 5,756,464, U.S. application Ser. No. 08/862,785 filed May 23, 1997 and corresponding International Publication No. WO 97/44056 (PCT/US97/08941), all of which are incorporated herein by reference), burn injury (as described in U.S. Pat. No. 5,494,896, which is incorporated herein by reference), ischemia/reperfusion injury (as described in U.S. Pat. No. 5,578,568, incorporated herein by reference), and liver resection (as described in co-owned, co-pending U.S. application Ser. No. 08/582,230 filed Jan. 3, 1996, which is in turn a continuation of U.S. application Ser. No. 08/318,357 filed Oct. 5, 1994, which is in turn a continuation-in-part of U.S. application Ser. No. 08/132,510 filed Oct. 5, 1993, and corresponding International Publication No. WO 95/10297 (PCT/US94/11404), all of which are incorporated herein by reference).

BPI protein products also neutralize the anti-coagulant activity of exogenous heparin, as described in U.S. Pat. No. 5,348,942, incorporated herein by reference, and are useful for treating chronic inflammatory diseases such as rheumatoid and reactive arthritis and for inhibiting angiogenesis and for treating angiogenesis-associated disorders including malignant tumors, ocular retinopathy and endometriosis, as described in U.S. Pat. Nos. 5,639,727, 5,807,818 and 5,837,678 and International Publication No. WO 94/20128 (PCT/US94/02401), all of which are incorporated herein by reference.

BPI protein products are also useful in antithrombotic methods, as described in U.S. Pat. No. 5,741,779 and U.S. application Ser. No. 09/063,465 filed Apr. 20, 1998 and corresponding WO 97/42967 (PCT/US97/08017), all of which are incorporated herein by reference.

SUMMARY OF THE INVENTION

The present invention provides novel therapeutic uses for BPI protein products for treatment (both prophylactic and therapeutic) of otitis media with effusion (OME) in humans, which results in amelioration of the clinical signs and symptoms, quicker resolution of the signs and symptoms, or a reduction in the occurrence, recurrence or severity of complications associated with the disease. Treatment of subjects with and without tympanostomy tubes is also contemplated.

It is contemplated that the administration of a BPI protein product may be accompanied by the concurrent administration of other known therapeutic agents appropriate for treating otitis media or OME, including histamine, corticosteroids, and antibiotics.

Use of a BPI protein product in the manufacture of a medicament for the treatment of OME is also contemplated.

Numerous additional aspects and advantages of the invention will become apparent to those skilled in the art upon consideration of the following detailed description of the invention which describes presently preferred embodiments thereof.

DETAILED DESCRIPTION OF THE INVENTION

The present invention provides novel therapeutic uses for BPI protein products for treatment of humans suffering from otitis media with effusion (OME), including recurrent or chronic OME. "Treatment" as used herein encompasses both prophylactic and therapeutic treatment. Treatment is expected to be effective even when the patient shows no signs of acute infection.

The invention thus contemplates methods for treating a human suffering from OME which comprise administering a therapeutically effective amount of a BPI protein product. Such an amount may be effective to ameliorate clinical signs and symptoms associated with OME, including impaired mucociliary clearance function, histological signs of inflammation or mucociliary system dysfunction, clinical signs of inflammation (including swelling that impinges on drainage through the eustachian tube), the accumulation or presence of effusion, reduced mobility of the tympanic membrane (e.g., as observed by pneumatic otoscope or as measured by tympanometry, which measures tympanic membrane stiffness [a tympanometric width of >250 dekaPascals (daPa) is considered diagnostic of OME]), hearing loss (e.g., as measured by an audiogram), especially hearing loss at high frequencies (e.g., >4000 Hz), local pain and discomfort, and other signs and symptoms. Such an amount may also be effective to more quickly resolve (e.g., reduce the duration of) these clinical signs and symptoms or to reduce the occurrence, recurrence or severity of complications associated with OME, including the development of chronic OME; recurrence of otitis media or OME; the need for myringotomy or placement of tympanostomy tubes; intratemporal complications such as drainage, chronic suppurative otitis media, tympanosclerosis, atrophy, tympanic membrane perforation or retraction, atelectasis, adhesive otitis media, cholesteatoma, facial nerve paralysis and destruction of ossicles; mastoid complications such as mastoiditis, mastoid abscess and petrositis; intracranial complications such as menigitis, lateral sinus thrombosis and extradural abscess; the potential speech, language, behavioral, cognitive or other developmental delays, potential learning disabilities, deficient expressive language skills, or deficient attention skills. Treatment with BPI protein product may assist in the re-establishment of the mucociliary clearance system, may render unnecessary a myringotomy procedure and/or the placement of tympanostomy tubes or may shorten the duration of tube placement. These advantages taken together result in reduced treatment costs and an improved quality of life.

The treatment of neonates, infants, toddlers and older children, as well as adults, whether healthy or suffering from accompanying illness or infection, is contemplated. Treatment is contemplated not only of subjects suffering from OME (in which an effusion in the middle ear is not accompanied by signs of acute infection), with or without the presence of tympanostomy or ventilation tubes; but also subjects suffering from recurrent OME or chronic OME (present at least three months). Further contemplated is treatment of subjects at risk for development of OME, including subjects with a small eustachian tube, subjects with otherwise impaired middle ear drainage (e.g. by impaired function of the mucociliary clearance system), subjects with chronic or recurrent episodes of OME, and subjects with other risk factors for a longer duration of OME (e.g., group child care, exposure to other children, smoke exposure, feeding in supine position, early onset of otitis media, several prior episodes of otitis media, or having a sibling suffering from otitis media).

The invention is based on the discovery that a BPI protein product, $rBPI_{21}$, was efficacious in a rat model of OME. An OME syndrome can be produced by a combination of eustachian tube obstruction and endotoxin injection. In this model of otitis media with effusion (OME), histological signs of mucociliary clearance system dysfunction include hyperproliferation of the epithelium, increases in secretory cells of the epithelium and degeneration of cilia, which result in a disturbance of the mucociliary clearance system of the middle ear. Endotoxin injection alone also disturbs the mucociliary clearance system but induces less morphological changes in the epithelial layer. As long as these morphological changes are present in the middle ear, the OME will continue. Therefore, re-establishment of the clearance system is expected to be an important step in treating ongoing OME or preventing recurring OME. In this model, injection of rBPI$_{21}$ directly into the middle ear two days or even as late as two weeks after OME induction protected the middle ear mucosa from morphological changes which may disturb the normal mucociliary clearance system of the middle ear and also inhibited the influx of PMNs and macrophages.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. The BPI protein products administered according to this invention may be generated and/or isolated by any means known in the art. U.S. Pat. No. 5,198,541, the disclosure of which is incorporated herein by reference, discloses recombinant genes encoding, and methods for expression of, BPI proteins including recombinant BPI holoprotein, referred to as rBPI and recombinant fragments of BPI. U.S. Pat. No. 5,439,807 and corresponding International Publication No. WO 93/23540 (PCT/US93/04752), which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include an N-terminal fragment of natural human BPI of approximately 25 kD, described in Ooi et al., *J. Exp. Med.*, 174:649 (1991), and the recombinant expression product of DNA encoding N-terminal amino acids from 1 to about 193 to 199 of natural human BPI, described in Gazzano-Santoro et al., *Infect. Immun.* 60:4754–4761 (1992), and referred to as rBPI$_{23}$. In that publication, an expression vector was used as a source of DNA encoding a recombinant expression product (rBPI$_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 1 and 2) set out in FIG. 1 of Gray et al., supra, with the exceptions noted for rBPI$_{23}$ and with the exception that residue 417 is alanine (specified by GCT) rather than valine (specified by GTT). A fragment consisting of residues 10–193 of BPI has been described in co-owned, co-pending U.S. application Ser. No. 09/099,725 filed Jun. 19, 1998, incorporated herein by reference. Other examples include dimeric forms of BPI fragments, as described in U.S. Pat. No. 5,447,913 and corresponding International Publication No. WO 95/24209 (PCT/US95/03125), all of which are incorporated herein by reference.

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described in U.S. Pat. No. 5,643,570 and corresponding International Publication No. WO 93/23434 (PCT/US93/04754), which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

Biologically active analogs of BPI (BPI analogs) include but are not limited to BPI protein products wherein one or more amino acid residues have been replaced by a different amino acid. For example, U.S. Pat. No. 5,420,019 and corresponding International Publication No. WO 94/18323 (PCT/US94/01235), all of which are incorporated herein by reference, discloses polypeptide analogs of BPI and BPI fragments wherein a cysteine residue is replaced by a different amino acid. A stable BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated rBPI$_{21}\Delta$cys or rBPI$_{21}$. Production of this N-terminal analog of BPI, rBPI$_{21}$, has been described in Horwitz et al., *Protein Expression Purification*, 8:28–40 (1996). Similarly, a fragment consisting of residues 10–193 of BPI in which the cysteine at position 132 is replaced with an alanine (designated "rBPI(10–193)C132A" or "rBPI (10–193)ala$^{132}$") has been described in co-owned, co-pending U.S. application Ser. No. 09/099,725 filed Jun. 19, 1998. Other examples include dimeric forms of BPI analogs; e.g. U.S. Pat. No. 5,447,913 and corresponding International Publication No. WO 95/24209 (PCT/US95/ 03125), all of which are incorporated herein by reference.

Other BPI protein products useful according to the methods of the invention are peptides derived from or based on BPI produced by synthetic or recombinant means (BPI-derived peptides), such as those described in International Publication No. WO 97/04008 (PCT/US96/03845), which corresponds to U.S. application Ser. No. 08/621,259 filed Mar. 21, 1996, and International Publication No. WO 96/08509 (PCT/US95/09262), which corresponds to U.S. Pat. No. 5,858,974, and International Publication No. WO 95/19372 (PCT/US94/10427), which corresponds to U.S. Pat. No. 5,652,332, and International Publication No. W094/ 20532 (PCT/US94/02465), which corresponds to U.S. Pat. No. 5,763,567 which is a continuation of U.S. Pat. No. 5,733,872, which is a continuation-in-part of U.S. application Ser. No. 08/183,222, filed Jan. 14, 1994, which is a continuation-in-part of U.S. application Ser. No. 08/093,202 filed Jul. 15, 1993 (corresponding to International Publication No. WO 94/20128 (PCT/US94/02401)), which is a continuation-in-part of U.S. Pat. No. 5,348,942, as well as International Application No. PCT/US97/05287, which corresponds to U.S. Pat. No. 5,851,802, the disclosures of all of which are incorporated herein by reference.

Presently preferred BPI protein products include recombinantly-produced N-terminal analogs and fragments of BPI, especially those having a molecular weight of approximately between 20 to 25 kD such as $rBPI_{21}$ or $rBPI_{23}$, rBPI(10–193)C132A (rBPI(10–193)ala$^{132}$), dimeric forms of these N-terminal proteins (e.g., $rBPI_{42}$ dimer), and BPI-derived peptides.

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants or other therapeutic agents. A stable pharmaceutical composition containing BPI protein products (e.g., $rBPI_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another stable pharmaceutical composition containing BPI protein products (e.g., $rBPI_{21}$) comprises the BPI protein product at a concentration of 2 mg/ml in 5 mM citrate, 150 mM NaCl, pH 5.0, 0.2% poloxamer 188 and 0.002% polysorbate 80. Such preferred combinations are described in U.S. Pat. Nos. 5,488,034 and 5,696,090 and corresponding International Publication No. WO 94/17819 (PCT/US94/01239), the disclosures of all of which are incorporated herein by reference. As described in U.S. application Ser. No. 08/586,133 filed Jan. 12, 1996, which is in turn a continuation-in-part of U.S. application Ser. No. 08/530,599 filed Sep. 19, 1995, which is in turn a continuation-in-part of U.S. application Ser. No. 08/372,104 filed Jan. 13, 1995, and corresponding International Publication No. WO096/21436 (PCT/US96/01095), all of which are incorporated herein by reference, other poloxamer formulations of BPI protein products with enhanced activity, with or without polysorbate, may be utilized.

Therapeutic compositions comprising BPI protein product may be administered systemically or topically. Systemic routes of administration include oral, intravenous, intramuscular or subcutaneous injection (including into a depot for long-term release), intraocular and retrobulbar, intrathecal, intraperitoneal (e.g. by intraperitoneal lavage), intrapulmonary (using powdered drug, or an aerosolized or nebulized drug solution), or transdermal. Topical routes include administration in the form of salves, ophthalmic drops, ear drops (e.g., for administration into the ear canal), irrigation fluids (for, e.g., irrigation of wounds) or medicated shampoos. For example, for topical administration in drop form, about 10 to 200 µL of a BPI protein product composition may be applied one or more times per day as determined by the treating physician.

When given parenterally, BPI protein product compositions are generally injected in doses ranging from 1 µg/kg to 100 mg/kg per day, preferably at doses ranging from 0.1 mg/kg to 20 mg/kg per day, more preferably at doses ranging from 1 to 20 mg/kg/day and most preferably at doses ranging from 2 to 10 mg/kg/day. The treatment may continue by continuous infusion or intermittent injection or infusion, at the same, reduced or increased dose per day for, e.g., 1 to 3 days, and additionally as determined by the treating physician.

Administration of BPI protein product for OME is preferably via instillation of a BPI protein product composition into the middle ear through the tympanic membrane, e.g., via a needle inserted for that purpose or via tympanostomy or ventilation tubes already in place, optionally preceded by withdrawal of existing effusion from the middle ear. The amount to be administered can be as much BPI protein product composition as may be accommodated in the middle ear, e.g., up to about 2 ml of fluid. The BPI protein product composition may contain BPI protein product at a concentration ranging from, e.g., 1 µg/mL to 10 mg/mL, or 0.2 to 2 mg/mL. The BPI protein product composition may be administered one time only as a single dose, or additional doses may be administered periodically, e.g., once weekly, once every two weeks, once every three weeks, or monthly, continuing until the desired effect is achieved. BPI protein product administration may also be accompanied by any surgical procedure deemed appropriate, e.g. myringotomy or tympanostomy tube placement.

Those skilled in the art can readily optimize effective dosages and administration regimens for therapeutic compositions comprising BPI protein product, as determined by good medical practice and the clinical condition of the individual subject. "Concurrent administration," or "co-administration," as used herein includes administration of the agents, in conjunction or combination, together, or before or after each other. The BPI protein product and second agent(s) may be administered by different routes. For example, the BPI protein product may be administered intravenously while the second agent(s) is(are) administered intravenously, intramuscularly, subcutaneously, orally or intraperitoneally. The BPI protein product and second agent(s) may be given sequentially in the same intravenous line or may be given in different intravenous lines. Alternatively, the BPI protein product may be administered in a special form for gastric delivery, while the second agent(s) is(are) administered, e.g., orally. The formulated BPI protein product and second agent(s) may be administered simultaneously or sequentially, as long as they are given in a manner sufficient to allow all agents to achieve effective concentrations at the site of action.

Other aspects and advantages of the present invention will be understood upon consideration of the following illustrative examples. Example 1A addresses the effect of BPI protein product on the signs and symptoms of OME when administered concurrently with endotoxin or two days after endotoxin. Example 1B addresses the effect of BPI protein product on the signs and symptoms of OME when administered two weeks after endotoxin. Example 2 addresses the effect of BPI protein product in humans suffering from OME.

EXAMPLE 1

Effect of BPI Protein Product on Otitis Media with Effusion

A. Treatment after Two Days

The effect of a BPI protein product, $rBPI_{21}$, was evaluated as follows in a rat model of chronic OME caused by eustachian tube obstruction in combination with endotoxin injection. Sixty-four female Wistar rats (body weight about 200 g, 10 weeks old) were divided into four control groups:

(1) control group (no injection), (2) injection control group treated with sterile pyrogen free phosphate buffered saline (PBS), (3) BPI control group treated with 2 mg/ml $rBPI_{21}$, and (4) endotoxin (E)/BPI group injected with 2 µg/ml endotoxin [from *Salmonella typhimurium*, Sigma, L6511] premixed (1:1) with 2 mg/ml $rBPI_{21}$ (E/BPI); and four experimental groups:

(1) E group, injected with 2 µg/ml endotoxin, (2) E+BPI group, treated with 2 mg/ml $rBPI_{21}$ after two days, (3) ETO+E group, which underwent eustachian tube obstruction (ETO) in combination with 2 µg/ml endotoxin injection (ETO+E), and (4) ETO+E+BPI group, which underwent ETO in combination with 2 μg/ml endotoxin injection followed by 2 mg/ml $rBPI_{21}$ injection after two days.

The rats were anesthetized with nitrous oxide, the Eustachian tube was accessed by a ventral approach, medially to the posterior belly of the digastric muscle, and was obstructed by plugging a small piece of Gelfoam® (Upjohn Co.) into the tube. Additionally, tissue glue (Historesin®) was used to keep the Gelfoam® in the tube. This procedure was directly followed by injection of the endotoxin and/or treatment solutions through the tympanic membrane until the solution overflowed. Injection of 50 μl of a solution of 2 μg/ml endotoxin results in a final concentration of approximately 100 ng endotoxin per ear.

After 1, 2, 4 or 12 weeks the animals were sacrificed with $CO_2$ gas and subsequently decapitated. The middle ear was dissected from the skull, denuded of adhering tissues and further processed for light microscopy and scanning electron microscopy. For light microscopy, the specimens were fixed with a solution of 1.5% glutaraldehyde in cacodylate buffer (0.14 M, pH 7.4), decalcified with a solution of 10% EDTA in 1.5% glutaraldehyde in cacodylate buffer (0.14M, pH 7.4) and subsequently dehydrated in a graded series of ethanols and embedded in glycol methacrylate (JB4, Brunschwig Chemie). Sections were stained with toluidine blue for histological studies and with Alcian Blue-PAS for glycoprotein histochemistry. In addition, two middle ears from each time period, prepared and fixed as described for light microscopy, were processed for scanning electron microscopy. The specimens were dehydrated in a graded series of ethanols and critical point dried using liquid $CO_2$. The distribution of the epithelial cells was studied with a Philips SEM 525M scanning electron microscope at 15 kV after mounting and coating with gold in a Balzers MED010 sputtercoater.

The numbers of ciliated and secretory goblet cells were counted in duplicate in each ear in standardized areas of the tympanic orifice of the Eustachian tube. The number of macrophages and PMNs, were counted in duplicate in each ear in the submucosal layer of the epitympanum and the hypotympanum of the middle ear bulla. To compare means of the different variables, one-way ANOVA Tukey's—HSD test with significance level P<0.05, was performed using the Statistical Package for the Social Science (SPSS). This test uses the studentized range statistic to make all of the pairwise comparisons between groups and sets the experimentwise error rate at the error rate for the collection for all pairwise comparisons. Results are reported as mean cell numbers ± standard error (SE).

The results of light- and scanning electron microscopy showed that control middle ears appeared normal during the entire treatment period. The hypotympanum of the middle ear consisted of thin, one-layered squamous epithelium, containing very few ciliated cells. In the tympanic orifice of the Eustachian tube a more pseudostratified, cuboidal or cylindrical epithelium (representing the mucociliary clearance system) was observed which contained an abundant number of ciliated cells and a few secretory cells. Inoculation of BPI induced a slight increase in goblet cells after one and twelve weeks but caused no morphological changes to the epithelial layer. In addition, some infiltration of PMNs in the middle ear cavity was observed, but these cells disappeared after two weeks. In comparison to the non-injected controls, the premixed solution of endotoxin and BPI did induce morphological changes in the middle ear. Injection of $rBPI_{21}$ into the middle ear cavity two days after the induction of OME prevented the induction of morphological changes to the mucociliary clearance system. BPI protein product administration at day two prevented the increases in secretory cells, the hyperproliferation of the epithelial layer and the infiltration of inflammatory cells into the subepithelial layer, and inhibited the formation of cobblestone-like cells. Furthermore, no deformation or degeneration of the cilia was observed in the BPI-treated group.

B. Treatment after Two Weeks

Twenty-four female Wistar rats (body weight about 200 g, 10 weeks old) were used in this study. They were divided into three control groups:

(1) untreated control group (no injections), (2) BPI control group injected with 2 mg/ml $rBPI_{21}$, and (3) BPI-buffer control group injected with BPI formulation buffer [5 mM citrate, 150 mM NaCl, pH 5.0, 0.2% poloxamer 188 and 0.002% polysorbate 80]; and two experimental groups:

(1) ETO+E group that underwent eustachian tube obstruction (ETO) in combination with injection of 2 μg/ml endotoxin, (2) ETO+E+BPI group that underwent ETO followed by injection of 2 mg/ml $rBPI_{21}$ after two weeks (ETO+E+BPI). The BPI protein product was injected directly into the middle ear cavity two weeks after the induction of OME to a final concentration of approximately 100μg per ear, which is approximately 1000 times the endotoxin concentration administered.

Animals were sacrificed after 4 or 12 weeks and their middle ears were prepared and analyzed as described above in Example 1A. Results are displayed in Table 1 below.

TABLE 1

|  | Cilia | | Goblet cells | | Macrophages | |
| --- | --- | --- | --- | --- | --- | --- |
|  | 4 wk | 12 wk | 4 wk | 12 wk | 4 wk | 12 wk |
| Untreated | 26 + 4 | 24 + 3 | 15 + 3 | 14 + 2 | 10 + 4 | 13 + 4 |
| $rBPI_{21}$ | 23 + 4 | 21 + 3 | 19 + 2 | 16 + 3 | 17 + 5 | 21 + 4 |
| BPI-buffer | 23 + 3 | 22 + 3 | 19 + 3 | 15 + 2 | 11 + 6 | 20 + 9 |
| ETO + E | 8 + 3* | 6 + 4* | 27 + 4* | 31 + 4* | 25 + 2* | 27 + 3* |
| ETO + E + $rBPI_{21}$ | 28 + 4** | 26 + 6** | 18 + 3** | 18 + 4** | 11 + 5** | 18 + 3 |

*represent values significantly different from untreated ears
**represent values significantly different from ETO + E of the same week In the untreated control group, at 12 weeks 14±2 secretory cells and 24±3 ciliated cells were counted. In the subepithelial layer of the hypotympanum and the epitympanum, at 12 weeks 13±4 macrophages were present.

In the BPI control groups, injection of either $rBPI_{21}$ or BPI formulation buffer into the middle ear cavity did not induce histological changes to the middle ear mucosa. In addition, no significant changes in the numbers of secretory cells nor in the number of ciliated cells were measured. Although the numbers of macrophages increased to 21±4 at 12 weeks after rBPI$_{21}$ injection, this was not significantly different from the untreated ears.

In the group with experimentally induced OME (ETO+E), obstruction of the eustachian tube in combination with endotoxin injection induced thickening of the middle ear mucosa. An important parameter of inflammation is the influx of polymorphonuclear cells (PMNs) and macrophages. After experimentally induced OME, a direct influx of PMNs occurs in the middle ear which gradually decreases followed by a gradual increase in macrophages. In the subepithelial layer a significant number of macrophages (27±3, at 12 weeks) were counted. The number of macrophages in the submucosal layer of the middle ear cavity was significantly higher than in the untreated ears at both 4 and 12 weeks. Furthermore, in the tympanic orifice a significant increase in the number of secretory cells (31±4) and a significant decrease in the number of ciliated cells (6±4) were measured at 12 weeks. With scanning electron microscopy it was observed that the epithelial cells in the hypotympanic part of the middle ear cavity contained an abundant number of microvilli and the surface was irregular and swollen. In the tympanic orifice, abnormalities in the MCS were observed, including large areas of secretory cells with sporadic mucus deposits and separation of some epithelial cells.

In the BPI treatment group (ETO+E+BPI), injection of rBPI$_{21}$ two weeks after induction of OME resulted in a normal thin squamous epithelium in the hypotympanum, which was not thickened and contained few microvilli. The number of macrophages was significantly decreased at 4 weeks (11±5 compared to 25±2 for ETO+E). At 12 weeks, the number of macrophages was decreased but not significantly different from ETO+E. In addition, in the tympanic orifice the numbers of secretory cells were significantly decreased at 4 and 12 weeks (18±4) compared to ETO+E. The numbers of ciliated cells were significantly increased at 4 weeks (28±4) and 12 weeks (26±6) compared to ETO+E. Both the number of ciliated and secretory cells and the number of macrophages were not significantly different from that of the untreated control group. Finally, with scanning electron microscopy the cilia in the tympanic orifice were observed to have a normal appearance and no mucus deposits or separation of epithelial cells were observed.

These results show that BPI protein product treatment two weeks after induction of OME inhibited the histological signs of MCS dysfunction and inhibited the influx of macrophages associated with this disease state. This result indicates that BPI protein product can re-establish the MCS function of the middle ear and is expected to be effective for treating OME.

EXAMPLE 2

Clinical studies are performed to test the effect of rBPI$_{21}$ in humans suffering from OME. A study is carried out generally as follows. Children suffering from OME, preferably chronic OME with recurrent otitis media, are divided into treatment and control groups. In the treatment group, BPI protein product is instilled into the middle ear, e.g. through existing ventilation tubes or via a needle injection. The children are then monitored for up to one month following treatment for, e.g., resolution of tympanic membrane stiffness as measured on a tympanogram, improvement in hearing, especially high frequency hearing, by audiogram, and time to resolution of these endpoints. Biopsies of middle ear epithelium to evaluate histological signs of MCS dysfunction may also be performed. Alternatively, rather than dividing the subjects into treatment and control groups, for each subject (with OME in both ears), one ear is the treatment ear and the other ear is the control ear. In another clinical study, treatment modalities are compared among several groups, e.g., (1) BPI protein product treatment with tube placement, (2) BPI protein product treatment without tube placement, (3) tube placement alone without BPI protein product treatment, and (4) no treatment and no tube placement. In further or ongoing clinical studies, repeat injections of BPI protein product are performed, e.g., every 1, 2, 3 or 4 weeks and the children continue to be monitored.

Numerous modifications and variations of the above-described invention are expected to occur to those of skill in the art. Accordingly, only such limitations as appear in the appended claims should be placed thereon.

What is claimed is:

1. A method of treating a human with otitis media with effusion in which an effusion in the middle ear is not accompanied by signs of acute infection comprising administering to said human a therapeutically effective amount of a bactericidal/permeability-increasing protein (BPI) protein product.

2. The method of claim 1 wherein the BPI protein product is rBPI$_{21}$.

3. The method of claim 1 wherein the BPI protein product is an N-terminal fragment of BPI having a molecular weight between 20 to 25 kd.

4. The method of claim 1 wherein the BPI protein product is rBPI(10–193)ala$^{132}$.

5. The method of claim 1 wherein the BPI protein product is recombinant BPI holoprotein (rBPI).

6. The method of claim 1 wherein the human has tympanostomy tubes placed in the middle ear.

* * * * *

UNITED STATES PATENT AND TRADEMARK OFFICE
CERTIFICATE OF CORRECTION

PATENT NO. : 6,670,327 B1
DATED : December 30, 2003
INVENTOR(S) : Grote et al.

It is certified that error appears in the above-identified patent and that said Letters Patent is hereby corrected as shown below:

<u>Title page,</u>
Item [75], Inventors, after "Jan J. Grote," please delete "RC Leiden" and insert -- Leiden -- in its place; and after "Maartje J. Nell," please delete "RC Leiden" and insert -- Leiden -- in its place.

Signed and Sealed this

Thirtieth Day of March, 2004

JON W. DUDAS
*Acting Director of the United States Patent and Trademark Office*